(12) United States Patent
Zeng

(10) Patent No.: US 7,600,441 B2
(45) Date of Patent: Oct. 13, 2009

(54) COMPREHENSIVE PARTICULATE MATTER MEASUREMENT SYSTEM AND METHOD FOR USING THE SAME

(75) Inventor: Yousheng Zeng, Plano, TX (US)

(73) Assignee: Providence Engineering and Environmental Group LLC, Baton Rouge, LA (US)

( * ) Notice: Subject to any disclaimer, the term of this patent is extended or adjusted under 35 U.S.C. 154(b) by 289 days.

(21) Appl. No.: 11/703,234

(22) Filed: Feb. 7, 2007

(65) Prior Publication Data

US 2007/0180936 A1    Aug. 9, 2007

Related U.S. Application Data

(60) Provisional application No. 60/766,712, filed on Feb. 7, 2006.

(51) Int. Cl.
*G01N 1/22* (2006.01)
(52) U.S. Cl. .................................... 73/865.5
(58) Field of Classification Search ............ 73/865.5, 73/61, 61.4
See application file for complete search history.

(56) References Cited

U.S. PATENT DOCUMENTS 3,628,139 A * 12/1971 Huber ................... 73/28.01

* cited by examiner

*Primary Examiner*—Hezron Williams
*Assistant Examiner*—Alex Devito
(74) *Attorney, Agent, or Firm*—Robert E. Bushnell, Esq.

(57) ABSTRACT

A comprehensive particulate matter measurement system (CPMMS) that measures accurate mass size distribution of particulate matter (PM) in ambient air, and a method to measure the accurate mass size distribution of PM are provided. The CPMMS includes a mass-based PM sampler, a particle sizing device, and an analysis system that manipulates data sent from the mass-based PM sampler and the particle sizing device to accurately measure mass size distribution of PM. The mass-based PM sampler measures total mass concentration of PM, and the particle sizing device measures size or volume size distribution of PM. Estimated total mass concentration is obtained from the size distribution predicting an assumed density of PM, and is compared with the actual total mass concentration measured by the mass-based PM sampler. A correct density of PM can be obtained from the actual total mass concentration, and as a result, accurate mass size distribution can be obtained.

19 Claims, 5 Drawing Sheets

COMPREHENSIVE PARTICULATE MATTER MEASUREMENT SYSTEM AND METHOD FOR USING THE SAME

CLAIM OF PRIORITY

This application claims priority under 35 U.S.C. §119 to Provisional Patent Application No. 60/766,712, entitled "COMPREHENSIVE PARTICULATE MATTER MEASUREMENT SYSTEM (CPMMS)" filed on the 7 Feb. 2006, which application is incorporated herein by reference.

BACKGROUND OF THE INVENTION

1. Field of the Invention

The present invention relates to a comprehensive particulate matter measurement system (CPMMS) that accurately measures mass size distribution of particulate matter (PM), and a method of the measurement of the mass size distribution of particulate matter using the comprehensive particulate matter measurement system.

2. Description of the Related Art

Particulate matter (PM) is one of the six criteria air pollutants with established national ambient air quality standards (NAAQS) in the United States. Unlike the other air pollutants, PM is not a single substance and is difficult to define due to its varying compositions and sizes of individual particles that make up PM. Currently PM is defined by sampling methods. For example, PM measured by a sampler with a cut point at an aerodynamic diameter of 2.5 µm is defined as $PM_{2.5}$. Current PM related health effect research and government regulations are based on such PM metrics as $PM_{2.5}$, $PM_{10}$, etc., which are based on somewhat arbitrary cut points and do not necessarily represent the PM portion that can be deposited onto human respiratory tract.

The regulatory definition and scope of airborne PM has been changed in the past decades from total suspended particulates (TSP) to PM with an aerodynamic diameter less than 10 µm ($PM_{10}$) and PM with an aerodynamic diameter less than 2.5 µm ($PM_{2.5}$). The U.S. Environmental Protection Agency is now considering an ambient standard for coarse particle (PMc) for particles with an aerodynamic diameter between 2.5 µm and 10 µm. Every time the PM definition and standard change, however, a new PM monitoring method must be developed to measure ambient PM levels accordingly.

Currently, $PM_{10}$ and $PM_{2.5}$ are normally monitored using the Federal Reference Methods (FRMs) described in Title 40, Code of Federal Regulations, Part 50 (40 CFR §50), Appendixes M and L, respectively. These methods are based on gravimetric measurement of PM mass collected on a filter and volume of air sampled. The PM samplers are specifically designed to measure a particular PM category as defined in the regulations and cannot be used for other PM categories. When the regulatory definition of PM and corresponding monitoring method change, the change disrupts the continuity of ambient PM monitoring data and creates difficulties for epidemiological studies on the human health effects of the ambient PM levels. It would be advantageous to develop a universal PM monitoring system that offers both mass concentrations in accuracy comparable to the existing FRM and particle size distribution so that the monitoring results can be expressed in more than one way in order to fit any current or future regulatory PM definitions.

Human health effects of ambient air PM levels are the primary concern in promulgating NAAQS for PM. Although it is common knowledge in the scientific community that the PM health effects are closely associated with certain PM size ranges and that these size ranges do not have clear-cut diameter boundaries, current PM samplers can only collect PM samples in a particular size range. Considering both the limitation of PM samplers and PM deposition curves for the human respiratory system available at the time, regulatory authorities have to choose a somewhat arbitrary diameter cut point such as 10 µm or 2.5 µm. As a result, the question of where to set the cut point diameter in PM regulatory definitions and standards is a very controversial issue in ambient air PM regulations.

SUMMARY OF THE INVENTION

It is therefore, an objective of the present invention to provide an improved process for comprehensive particulate matter measurement and an improved process for comprehensive particulate matter measurement system.

It is another object to provide a comprehensive particulate matter measurement system (CPMMS) that can replace the current particulate matter (PM) measurement systems and can provide accurate ambient PM mass size distribution. Embodiments of the present invention are also able to provide a method to accurately measure the ambient PM mass size distribution.

The data produced by the present invention can be reprocessed to yield various PM metrics to meet research and regulatory needs. The new system is not based on an arbitrary cut point and it represents the portion of PM that can actually be deposited in a human respiratory tract. This process is not limited to measure particles in ambient air. It can be used to measure particles suspended in indoor air, process air, or in any other fluids in general.

The method of measuring particulate matter (PM) and the comprehensive particulate matter measurement system contemplated by the present invention make the PM monitoring system comprehensive (yielding both mass concentrations and mass size distributions) and valid even if the regulatory definition of PM changes, assess the potential biases inherent to various PM measurement methods, and provide a framework to establish PM regulatory definitions and standards based on the portion of PM that actually deposits in the human respiratory system without using a somewhat arbitrary cut point diameter. This approach of dosimetry based PM metrics and standards is designed to make the PM standards linked to human health effects closer than the current standards and to make it unnecessary to define PM on the basis of a particular cut point diameter.

According to an embodiment of the present invention, a method of measuring mass size distribution of particulate matter is provided. The method includes steps of sampling particulate matter, measuring an actual total mass concentration of the particulate matter, measuring a size distribution of the particulate matter, obtaining an estimated total mass concentration of the particulate matter from the measured size distribution of the particulate matter, comparing the estimated total mass concentration with the actual total mass concentration, obtaining a correct density of the particulate matter, and obtaining an actual mass size distribution of the particulate matter from the correct density.

In this method, the step of measuring the actual total mass concentration can be performed by a mass-based particulate sampler, and the step of measuring of the size distribution can be performed by a particle sizing device.

The step of obtaining an estimated total mass concentration includes steps of predicting an assumed density of the particulate matter, and obtaining an assumed mass size distribution from the size distribution and the assumed density. The step of obtaining the estimated total mass concentration also can include steps of simulating a sampling effectiveness of a mass-based particulate matter sampler, obtaining an assumed mass size distribution from the size distribution, and calculating the estimated total mass concentration.

According to another embodiment of the present invention, a comprehensive particulate matter measurement system for measuring mass size distribution of particulate matter is provided. The comprehensive particulate matter measurement system includes a mass-based particulate matter sampler for measuring an actual total mass concentration of the particulate matter, a particle sizing device for measuring a size distribution of the particulate matter, and an analysis system including an analysis system readable storage medium. The analysis system is coupled to each of the mass-based particulate matter sampler and the particle sizing device. The readable storage medium provides instructions that cause the analysis system to perform operations to obtain a mass size distribution of the particulate matter.

According to another embodiment of the present invention, a machine readable storage medium causing a machine to execute processes for obtaining a mass size distribution of particulate matter is provided. The machine readable storage medium provides instructions that cause the machine to perform operations to obtain a mass size distribution of particulate matter. The operations includes operations of causing the machine to receive an actual total mass concentration of the particulate matter, causing the machine to receive a size distribution of the particulate matter, obtaining an estimated total mass concentration of the particulate matter from the size distribution of the particulate matter, comparing the estimated total mass concentration with the actual total mass concentration, obtaining a correct density of the particulate matter, and obtaining an actual mass size distribution of the particulate matter from the density.

BRIEF DESCRIPTION OF THE DRAWINGS

A more complete appreciation of the invention, and many of the attendant advantages thereof, will be readily apparent as the same becomes better understood by reference to the following detailed description when considered in conjunction with the accompanying drawings in which like reference symbols indicate the same or similar components, wherein.

DETAILED DESCRIPTION OF THE INVENTION

The present invention will now be described more completely with reference to the accompanying drawings, in which an exemplary embodiment of the invention is shown.

Figure 5:
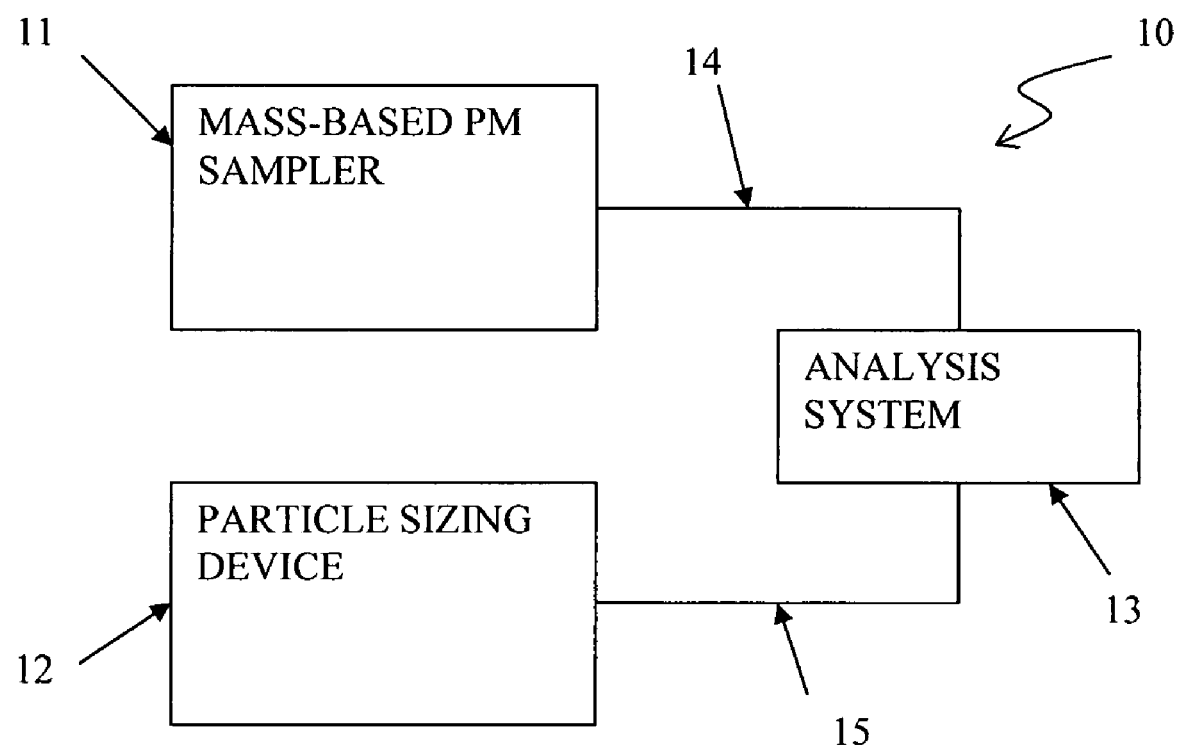
FIG. 5 shows a comprehensive particulate matter measurement system constructed as an embodiment of the present invention.

FIG. 5 shows a comprehensive particulate matter measurement system constructed as an embodiment of the present invention. Referring to FIG. 5, comprehensive particulate matter measurement system (CPMMS) 10 includes mass-based particulate matter (PM) sampler 11, particle sizing device 12, and analysis system 13 that includes an algorithm to measure the PM mass size distribution. Analysis system 13 may be implemented with either software or firmware that includes the algorithm.

Mass-based particulate matter (PM) sampler 11 measures mass concentration (typically in a unit of $\mu g/m^3$) of PM. The result is an aggregated (or total) mass concentration over the sampler's designed size range (e.g., 0-2.5 μm for FRM $PM_{2.5}$). Mass-based particulate matter (PM) sampler 11 involves a pump pulling ambient air sample through a sample inlet, a device designed to separate certain sizes of particles based on different aerodynamic behavior of particles in different sizes, and a filter to catch the particles in the desired size range. The mass-based PM sampler can be Federal Reference Method (FRM) for $PM_{2.5}$, FRM for $PM_{10}$, a continuous dichotomous sampler, etc. An example of the mass-based PM sampler can be found in Title 40, Code of Federal Regulations, Part 50 (40 CFR 50) Appendix L. Specifically, an example of a mass-based PM sampler for $PM_{10}$ is Andersen Instruments, Incorporated Model RAAS10-100 Single Channel Reference Method $PM_{10}$ Sampler, and an example of a mass-based PM sampler for $PM_{2.5}$ is Andersen Instruments, Incorporated Model RAAS2.5-200 PM2.5 Audit Sampler. The mass-based PM samplers, however, do not generate any size distribution data.

Particle sizing device 12 can be any of the various instruments that can be used to analyze non-mass-based particle size distributions, which includes volume size distribution, number size distribution, area size distribution, etc. In an embodiment of the present invention, particle sizing device 12 measures volume size distribution, but is not limited to the device that measures volume size distribution. Particle sizing device 12 can be any device that measures non-mass-based size distribution depending on applications. Some of these instruments are based on aerodynamic behavior of particles; others are based on light scattering or other characteristics of particles. An aerodynamic particle sizer (APS) made by TSI Inc. and nephelometers are some examples of these instruments potentially usable in the CPMMS.

Particle sizing device 12 by itself can not produce mass size distribution. To estimate mass size distributions, the current practice is to use a particle sizing device to obtain particle volume size distributions based on particle aerodynamic or optical properties, and to derive mass size distributions from the volume size distribution by assuming a particle density (e.g., a particle density of 2 grams per cubic centimeter or 2 g/cc). The mass size distributions obtained in this method are not reliable because the particle density assumption is not reliable.

More specifically, the particle sizing device measures initial particle volume size distribution for each particle size interval (e.g., 0-0.523 μm, 0.523-0.542 μm, 0.542-0.583 μm, etc.). The desired mass size distribution, which results in a unit of $\mu g/m^3$, are derived based on an assumed particle density (e.g., 2 g/cc). This arbitrary assumption makes the results unreliable in the absolute sense of mass size distribution, and unsuitable for estimating an aggregated mass concentration over a particle size range per regulatory definition. However, the relative mass distribution (in a unit of $\mu g/m^3$) between particle size intervals is much more reliable.

In the present invention, the two instruments, mass-based PM sampler 11 and particle sizing device 12, are integrated with analysis system 13 to form comprehensive particulate matter measurement system (CPMMS) 10. Analysis system 13 can be a computer or any custom designed machine, which can be coupled to the mass-based PM sampler and the particle sizing device. An algorithm for processing steps to measure mass size distribution of PM is implemented in analysis system 13. If the analysis system has a driver for reading a medium, the algorithm for the processes can be implemented in a readable medium that can be accessed by analysis system 13.

More specifically, analysis system 13 can be a computer communicating with mass-based PM sampler 11 and particle sizing device 12 through first connection member 14 and second connection member 15, respectively. First and second connection members 14 and 15 can be USB, serial cables, or any members that can achieve communications between mass-based PM sampler 11 and analysis system 13 and between particle sizing device 12 and analysis system 13, respectively. In this configuration, there will be three separate boxes, a PM sampler box, a sizing device box, and a computer box. We can select the PM sampler models and particle sizing models that can output the results through either USB or serial cables to the computer. The computer will use the CPMMS algorithm to generate the final results. The CPMMS algorithm can be added to the CPMMS as a form of a program. The program may be stored in the computer's hard drive, or can be provided from a computer readable storage medium.

Some models of particle sizing devices and PM samplers already have an onboard computer. In this case, the CPMMS algorithm can be added to the existing onboard computer. The algorithm can be added as a form of a program stored in the onboard computer's element such as memory chips. There will be only one cable to connect the PM sampler and the particle sizing device.

The CPMMS of the present invention also can be built by integrating the three instruments: mass-based PM sampler 11, particle sizing device 12, and analysis system 13. In this case, analysis system 13 can be an onboard computer (e.g., Motorola Power PC 860 processor running an embedded version of Linux operating system) that will not only control the particle sizing component and the mass-based PM sampling component; but also process the data according to the CPMMS algorithm.

Figure 1:
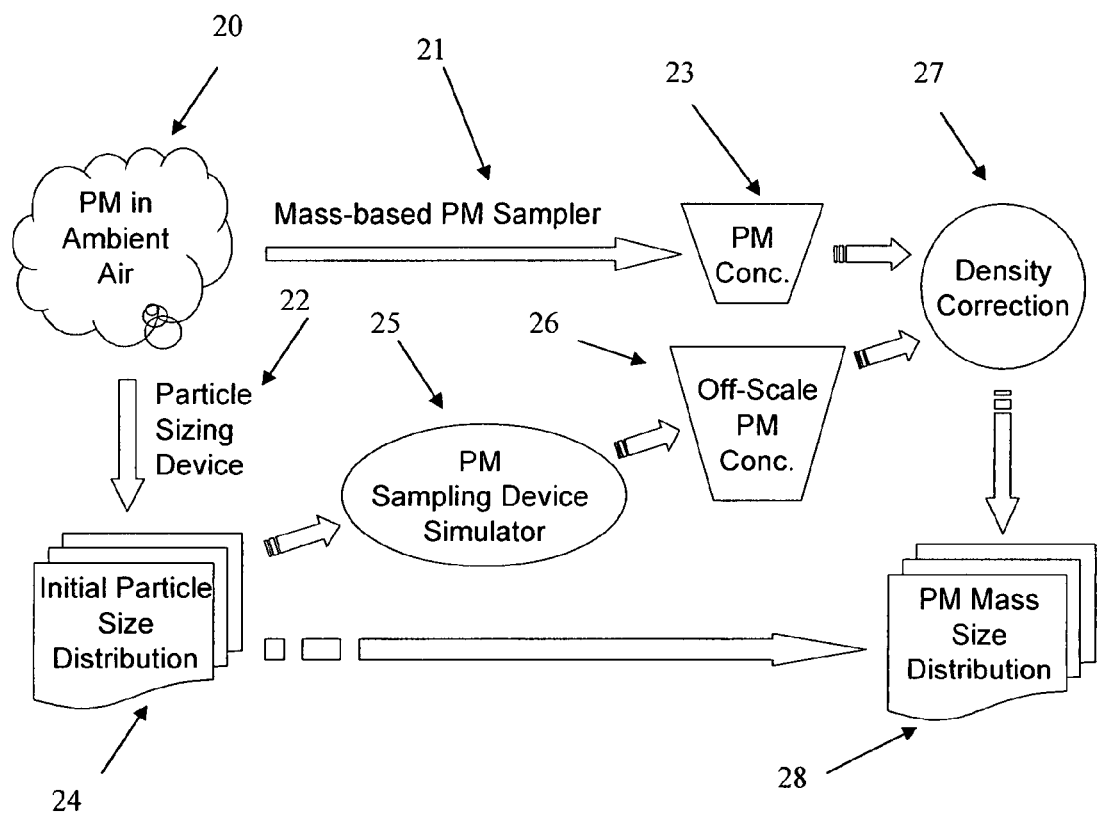
FIG. 1 schematically illustrates a comprehensive particulate matter measurement system and processes of measuring mass size distribution of particulate matter.

FIG. 1 schematically illustrates a comprehensive particulate matter measurement processes of measuring mass size distribution of particulate matter. Referring to FIG. 1, PM in ambient air 20 is collected in mass-based PM sampler 21 and particle sizing device 22. Mass-based PM sampler 21 measures PM mass concentration 23 (or actual mass concentration typically measured in a unit of $\mu g/m^3$) of the PM sample, which is collected by mass-based PM sampler 21, based on effectiveness curve (aspiration curve and fractionation curve) of mass-based PM sampler The result is an aggregated (or total) mass concentration over the sampler's designed size range (e.g., 0-2.5 μm for FRM $PM_{2.5}$).

Initial particle size distribution 24 of PM in ambient air 20 is measured by a particle sizing device 22. The initial particle size distribution measured by the particle sizing device virtually passes through PM sampling device simulator 25, resulting in off-scale PM mass concentration 26. This result is compared with the actual mass concentration determined by the mass-based PM sampler to yield a proper scaling factor. Off-scale PM mass concentration 26 is obtained by predicting an assumed density of PM, and a correct density of PM can be obtained by comparing off-scale PM mass concentration 26 with the actual mass concentration 23, which is represented as density correction 27 in FIG. 1. Once the correct density of PM is obtained, accurate actual PM mass size distribution 28 is obtained by applying the density correction 27 to the initial size distribution 24. The correct density of the PM can be applied to each size interval of the initial (or assumed) mass size distribution of the PM without repeating the calibration process.

With the scaling factor, the initial mass size distribution is corrected to a more accurate mass size distribution. In other words, in CPMMS, the actual aggregated (or total) mass concentration result obtained by the mass-based PM sampler is used to calibrate the results of the particle sizing device to produce accurate PM monitoring data in terms of mass size distribution and aggregation over any size ranges. In order to accomplish the calibration, CPMMS includes a CPMMS algorithm that is coupled to the mass-based PM sampler and the particle sizing device. The process of the calibration will be described later in detail referring to FIG. 2.

Once the mass size distribution is obtained, various dosimetry-based PM metrics can be determined by multiplying each interval mass concentration in the mass size distribution by the particle deposition fraction of corresponding size interval in certain region or the entire human respiratory tract, and by summing up the results of each size interval over the entire size range. For example, a dosimetry-based PM can be defined and calculated for PM that can actually deposit onto the tracheobronchial region of the human respiratory tract. An epidemiology study based on such dosimetry-based PM rather than current $PM_{2.5}$ or $PM_{10}$ is expected to be more meaningful and useful. Regulations based on this system are more protective of human health and cost effective (regulating the portion of PM that has health effects).

If the comprehensive particulate matter measurement system (CPMMS) is implemented as a new way of managing ambient air quality for PM, high quality mass size distribution data can be obtained. The mass size distribution data will be available to regenerate various dosimetry-based PM concentrations for different research purposes, e.g., an epidemiological study on ambient PM level defined by particle deposition in the tracheobronchial region of the human respiratory tract. Studies based on such PM data are expected to have closer correlations between PM data and epidemiological data, and will be more meaningful than those based on current PM data. Regulatory authorities can also establish dosimetry-based PM standards using human respiratory PM deposition data that are representative of and protective to selected groups of population (e.g., children).

In addition to ambient air quality monitoring, the CPMMS can be used to analyze or monitor particle mass size distributions for any industrial processes that deal with fine particulate materials.

Figure 2:
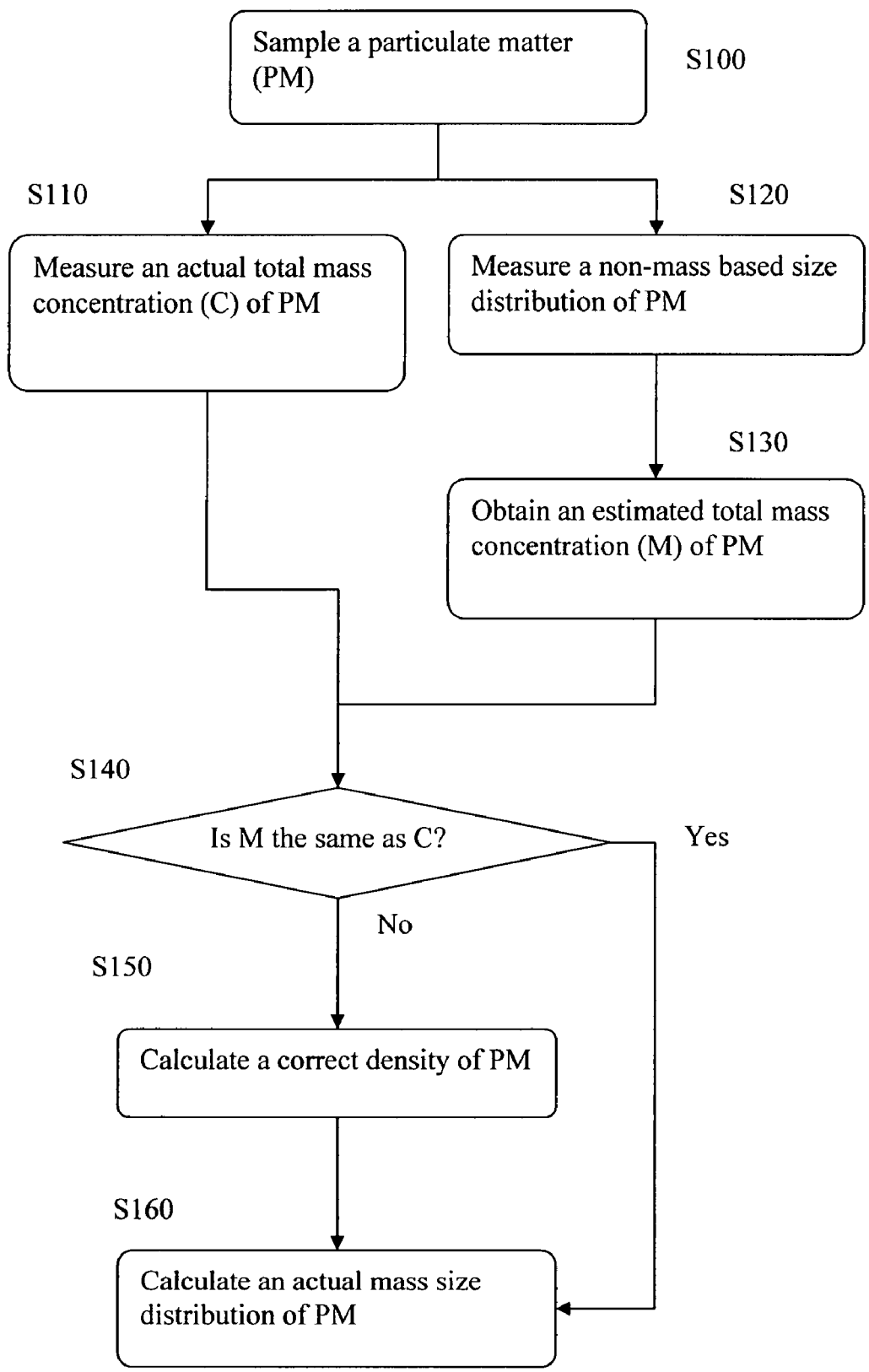
FIG. 2 schematically illustrates steps for the measurement of accurate mass size distribution of particulate matter.

FIG. 2 schematically illustrates steps for the measurement of accurate mass size distribution of particulate matter. First in step S100, PM in ambient air is collected and is sampled by a mass-based particulate matter (PM) sampler and a particle sizing device. In step S110, actual total mass concentration (C) of PM that is collected in the mass-based PM sampler is measured. The measured actual total mass concentration (C) will be used in step S150 to calibrate the results obtained from the particle sizing device.

In step S120, size distribution of PM is measured by the particle sizing device. If an aerodynamic particle sizer (APS) is used as a particle sizing device, volume size distribution of PM can be measured. Using an assumed density of the PM, the volume size distribution of PM can be converted into assumed mass size distribution of PM. The assumed mass size distribution of the PM, however, may not be correct, because it is based on the assumed density of the PM. At this step, the accuracy issue can be ignored, and the assumed mass size distribution of the PM is inputted into a mass-based PM sampling simulator.

In the step S130, an estimated total mass concentration (M) is obtained by running a mass-based PM sampling simulator. The processes of calculating the estimated total mass concentration will be herein described in detail.

Figure 3:
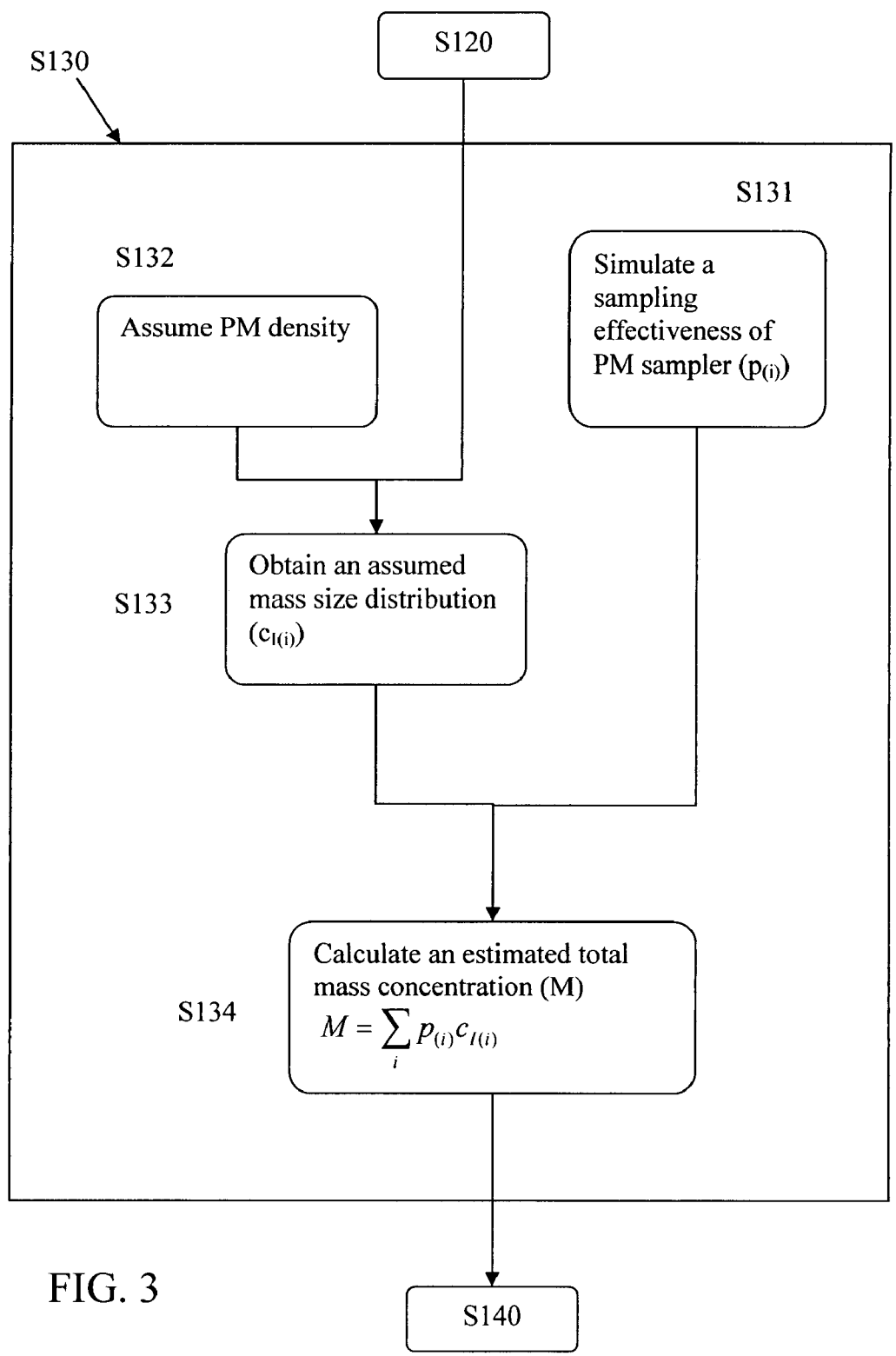
FIG. 3 specifically illustrates steps for obtaining an estimated total mass concentration of particulate matter.

FIG. 3 specifically illustrates steps for obtaining an estimated total mass concentration of particulate matter (S130). A mass-based PM sampler can be characterized by its sampling effectiveness curve. In order to obtain an estimated total mass concentration of PM, sampling effectiveness is simulated in step S131. The sampling effectiveness curves can be modeled using the following Equation 1.

$$p_{(i)} = \frac{1}{1 + [D_{(i)}/D_{50}]^n}$$ Equation 1 where $p_{(i)}$ is sampling effectiveness (or penetration) for particles in size interval i, $D_{(i)}$ a representative aerodynamic diameter of particles in size interval i, $D_{50}$ a sampler cutpoint diameter (particle aerodynamic diameter corresponding to 50% penetration), and n a number determining the steepness of the sampling effectiveness curve. Unit of $p_{(i)}$ can be % or fraction, and units of $D_{(i)}$ and $D_{50}$ are μm.

PM samplers can be simulated in the above model represented by Equation 1 by selecting proper values of two parameters, $D_{50}$ and n, using the least square approach. The accuracy of the simulation can be evaluated by virtually passing the idealized ambient particles as specified in 40 CFR 53 through the model (i.e., simulated sampler) and calculating the sum of the squared deviations of the model predicted values from the true values specified in 40 CFR 53. The results of the least square approach are normalized to be expressed as percent of the total PM mass of idealized ambient particle samples.

Figure 4:
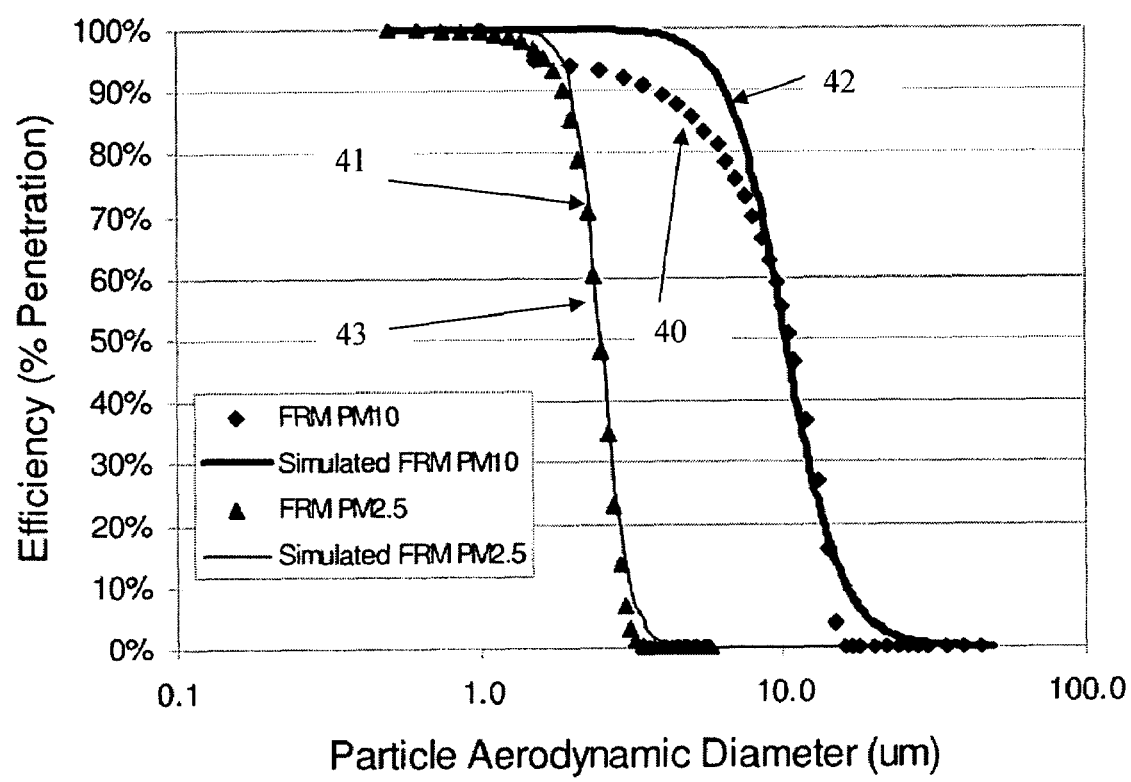
FIG. 4 shows sampling efficiency curves of mass-based PM samplers of FRM $PM_{10}$ and FRM $PM_{2.5}$ based on specifications in 40 CFR 53 Subpart D Table D-3 and Subpart F Table F-4, respectively, and simulated curves for FRM $PM_{10}$ and FRM $PM_{2.5}$.

FIG. 4 shows sampling efficiency curves of mass-based PM samplers of FRM $PM_{10}$ and FRM $PM_{2.5}$ based on specifications in 40 CFR 53 Subpart D Table D-3 and Subpart F Table F-4, respectively, and fitted curves simulated using Equation 1 for FRM $PM_{10}$ and FRM $PM_{2.5}$. In FIG. 4, data points represented by diamond marks 40 and triangular marks 41 represent the sampling efficiency curve of FRM $PM_{10}$ and FRM $PM_{2.5}$, respectively. Thick sold curve 42 and thin solid curve 43 represent simulation results for the sampling efficiency curves of FRM $PM_{10}$ and FRM $PM_{2.5}$, respectively. Simulation curve 42 for FRM $PM_{10}$ is obtained when $D_{50}$ is 10.0 μm and n is 4.6 in Equation 1, and simulation curve 43 for FRM $PM_{2.5}$ is obtained when $D_{50}$ is 2.5 μM and n is 10 in Equation 1. The selected values of the parameters, $D_{50}$ and n, are to demonstrate how to fit the sampling effectiveness curves of FRM $PM_{10}$ and FRM $PM_{2.5}$, and the curve fitting process of the present invention is not limited to these values presented in this paragraph. In other words, other values of $D_{50}$ and n can be selected to simulate other mass-based PM samplers.

As shown in FIG. 4, the simulated curves for FRM $PM_{10}$ and FRM $PM_{2.5}$ are well fitted to the actual curves of FRM $PM_{10}$ and FRM $PM_{2.5}$, which suggests that the model represented by Equation 1 can be used for the mass-based PM sampling simulator.

With the mass-based PM sampling simulator established as Equation 1, the initial particle size distribution data can be processed by the simulator. Referring to FIG. 3 again, an assumed density of the PM is predicted in step S132, and an initial (or assumed) mass size distribution of the PM is calculated in step S133. The assumed mass size distribution is obtained from the assumed density of the PM predicted in step S132 and the volume size distribution of the PM measured in step S120. The assumed particle mass size distribution data consist of assumed mass distribution in a unit of μg/m³ for each particle size interval. However, the value of the assumed mass size distribution may not be correct, because it is based on the assumed density for the PM predicted in step S132. At this step of the process, the accuracy issue of the assumed density can be ignored, and the assumed mass size distribution is further processed in next steps. In step S134, the simulator calculates an estimated total mass concentration of PM based on the assumed mass size distribution obtained in step S133 and sampling effectiveness curve simulated in step S131. The estimated total mass concentration of PM is obtained by the following Equation 2.

$$M = \sum_i m_{(i)} = \sum_i p_{(i)} c_{I(i)}$$ Equation 2 where M is an estimated total mass concentration of PM obtained by the simulated PM sampler, $m_{(i)}$ an estimated mass distribution of PM as collected on the sampler filter (i.e., passed sampler inlet cut) for size interval i, and $c_{I(i)}$ an assumed mass size distribution obtained in step 133 for size interval i. Units of M, $m_{(i)}$, and $c_{I(i)}$ are μg/m³.

Referring to step S140 of FIG. 2, after the estimated total mass concentration of the PM is obtained in step S130, the estimated total mass concentration (M) of the PM is compared with the actual total mass concentration (C) of the PM that is measured by the mass-based PM sampler in step S110. If the initial particle size distribution, $c_{I(i)}$, is accurate (i.e., the assumption of particle density is correct), the value of M should be the same as the actual total mass concentration (C) of the PM measured by the mass-based PM sampler. In this case, the process moves to step S160, and the assumed mass size distribution $c_{I(i)}$ is the same as the actual mass size distribution $c_{(i)}$.

If the estimated total mass concentration (M) is not the same as the actual total mass concentration (C) of the PM, the process moves to step S150 to calculate a correct density of the PM. The correct density of the PM can be derived using the following Equation 3.

$$\rho = \rho_A \frac{C}{M}$$ Equation 3 where ρ is a correct density of PM, $\rho_A$ an assumed density of PM, and C an actual total mass concentration of PM measured by the mass-based PM sampler. Units of ρ and $\rho_A$ are μg/m³, and units of C and M are g/cm³.

When an aerodynamic particle sizer (APS) is used to measure particle size distribution, it actually measures the aerodynamic diameters of individual particles using flight time of the particles. The aerodynamic diameters are used to calculate the volumes of the particles to obtain the volume size distribution. The assumed mass size distribution is finally calculated from the volume size distribution by assuming a particle density. The assumed mass size distribution is obtained from the following Equation 4.

$$c_{I(i)} = 10^6 v_{(i)} \rho_A$$ Equation 4 where $10^6$ is a conversion factor ($10^6$ μg/g), and $v_{(i)}$ a volume concentration measured by the particle sizing device for size interval i. Unit of $v_{(i)}$ is cm³/m³ (volume of particles/volume of air sample).

Therefore, once the correct density of the PM is known, the actual mass size distribution $c_{(i)}$ can be obtained in step S160 from the following Equation 5.

$$c_{(i)} = 10^6 v_{(i)} \rho \qquad \text{Equation 5}$$

where $c_{(i)}$ is an actual mass size distribution of PM for size interval i. Unit of $c_{(i)}$ is μg/m³.

Combining Equations 3, 4, and 5 can yield the following Equation 6 that can be used to calculate actual mass size distribution.

$$c_{(i)} = c_{I(i)} \frac{C}{M} \qquad \text{Equation 6}$$

Once an accurate actual mass size distribution ($c_{(i)}$) is obtained, any aggregated ambient PM monitoring data can be derived by summing up the $c_{(i)}$ over the desired size range. For example, a total mass concentration of PM in a certain range of particle size can be obtained as shown in Equation 7.

$$C = \sum_i c_{(i)}. \qquad \text{Equation 7}$$

If the summation shown in Equation 7 is done for intervals of mass $c_{(i)}$ representing particle diameters from 0 to 2.5 μm, the resulting C is $PM_{2.5}$. If the diameter range is from 2.5 μm to 10 μm, the resulting C is PMc or $PM_{10-2.5}$, etc.

If it is desired to have PM results that mimic a particular PM sampler, the actual mass size distribution ($c_{(i)}$) produced by CPMMS can again be used through a simulator of a desired PM sampler with sampling effectiveness curve represented by $p_{(i)}$ as shown in Equation 8.

$$C = \sum_i p_{(i)} c_{(i)} \qquad \text{Equation 8}$$

As shown above, once accurate mass size distribution is obtained as shown in Equation 6, PM measurement metrics can be defined (and reconstructed) by exact cut point (as seen in Equation 7), by sampler sampling effectiveness curve (Equation 8), or by PM deposition fraction of human respiratory system. The last one is dosimetry-based PM metrics, which is most relevant and meaningful. The dosimetry-based PM metrics, for example, can be calculated by the following Equation 9.

$$C_D = \sum_i d_{(i)} c_{(i)} \qquad \text{Equation 9}$$

where $C_D$ is dosimetry-based ambient PM concentration in a unit of μg/m³, $d_{(i)}$ respiratory tract (or a region of it) deposition fraction on a mass basis for size interval i, $c_{(i)}$ a mass size distribution of ambient PM for size interval i in a unit of μg/m³.

The processes for obtaining an accurate mass size distribution of PM are described so far. The process can be realized as a form of an algorithm that can be implemented as software or firmware, which can control a machine to execute the required processes. The comprehensive particulate matter measurement system (CPMMS) of the present invention includes a mass-based PM sampler, a particle sizing device, and an analysis system. An algorithm for processing the steps shown in FIGS. 2 and 3 can be implemented in the analysis system. The analysis system can be a computer or any custom designed machine, which can be coupled to the mass-based PM sampler and the particle sizing device, and which can execute the processes presented in the algorithm.

If the analysis system has a driver for reading a medium, the processes can be implemented in a readable medium that can be accessed by the analysis system. The medium can be any member such as a storage medium or memory, which can store the processes in a form of software, firmware, or any form that can be read by the analysis system. In this case, the medium includes portions or units that control the analysis system to execute necessary processes to obtain an accurate mass size distribution of PM. The medium also can include command portions that cause the analysis system to communicate with the mass-based PM sampler or the particle sizing device. The communication, for example, can be performed to read data from the mass-based PM sampler or the particle sizing device.

If the comprehensive particulate matter measurement system (CPMMS) is implemented as a new way of managing ambient air quality for PM, the results will be high quality mass size distribution data. The mass size distribution data will be available to regenerate various dosimetry-based PM concentrations for different research purposes, e.g., an epidemiological study on ambient PM level defined by particle deposition in the tracheobronchial region of the respiratory tract using Equation 9 and the related health impact. Studies based on such PM data will be more meaningful than those based on current PM data. Regulatory authorities can also establish dosimetry-based PM standards using human respiratory PM deposition data that are representative of and protective to selected groups of population (e.g., children).

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A method of measuring mass size distribution of particulate matter, comprising:

sampling particulate matter;

measuring an actual total mass concentration of the particulate matter using a mass-based particulate matter sampler;

measuring a non-mass-based size distribution of the particulate matter;

simulating the mass-based particulate matter sampler;

obtaining an estimated total mass concentration of the particulate matter based on the measured non-mass-based size distribution of the particulate matter and the simulated mass-based particulate matter sampler;

comparing the estimated total mass concentration with the actual total mass concentration;

obtaining a correct density of the particulate matter, and obtaining an actual mass size distribution of the particulate matter from the correct density.

2. The method of claim 1, comprised of the step of measuring of the non-mass-based size distribution being performed by a particle sizing device.

3. The method of claim 1, comprised of the step of obtaining an estimated total mass concentration comprising steps:
   predicting an assumed density of the particulate matter; and
   obtaining an assumed mass size distribution of the particulate matter based on the non-mass-based size distribution and the assumed density.

4. The method of claim 3, comprised of the correct density of the particulate matter being derived from a formula, $\rho = \rho_A C / M$, where $\rho$ is the correct density of the particulate matter, $\pi_A$ the assumed density sued by the particle sizing device, C the actual total mass concentration, and M the estimated total mass concentration.

5. The method of claim 3, comprised of the step of simulating the mass-based particulate matter sampler including a step of simulating a sampling effectiveness of the mass-based particulate matter sampler, and comprised of the step of obtaining the estimated total mass concentration comprising a step of calculating the estimated total mass concentration from a formula $$M = \sum_i p_{(i)} c_{I(i)}$$

where M is the estimated total mass concentration, $p_{(i)}$ the sampling effectiveness of the mass-based particulate matter sampler in size interval i, and $C_{I(i)}$ the assumed mass size distribution in size interval i.

6. The method of claim 5, comprised of the sampling effectiveness being simulated by a formula $$p_{(i)} = \frac{1}{1 + [D_{(i)}/D_{50}]^n}$$

where $P_{(i)}$ is the sampling effectiveness of the mass-based particulate matter sampler in size interval i, $D_{(i)}$ a representative aerodynamic diameter of particles in size interval i, $D_{50}$ a sampler cut point diameter, and n a parameter determining the steepness of the sampling effectiveness.

7. The method of claim 3, comprised of the step of obtaining actual mass size distribution of particulate matter by a formula $$c_{(i)} = c_{I(i)} \frac{C}{M}$$

where $c_{(i)}$ represents the actual mass size distribution of the particulate matter in size interval i, $c_{I(i)}$ the assumed mass size distribution the particulate matter in size interval i, C the actual total mass concentration of the particulate matter, and M the estimated total mass concentration of the particulate matter.

8. A comprehensive particulate matter measurement system for measuring mass size distribution of particulate matter, comprising:
   a mass-based particulate matter sampler for sampling particulate matter and for measuring an actual total mass concentration of the particulate matter;
   a particle sizing device for measuring a non-mass-based size distribution of the particulate matter; and
   an analysis system including an analysis system readable storage medium; the analysis system being coupled to each of the mass-based particulate matter sampler and the particle sizing device; the storage medium providing instructions that cause the analysis system to perform operations to obtain a mass size distribution of the particulate matter; the operations comprising:
      causing the analysis system to receive the actual total mass concentration of the particulate matter from the mass-based particulate matter sampler;
      causing the analysis system to receive the non-mass-based size distribution of the particulate matter from the particle sizing device;
      simulating the mass-based particulate matter sampler;
      obtaining an estimated total mass concentration of the particulate matter based on the non-mass-based size distribution of the particulate matter and the simulated mass-based particulate matter sampler;
      comparing the estimated total mass concentration with the actual total mass concentration;
      obtaining a correct density of the particulate matter; and
      obtaining an actual mass size distribution of the particulate matter from the correct density.

9. The comprehensive particulate matter measurement system of claim 8, comprised of the step of simulating the mass-based particulate matter sampler including a step of simulating a sampling effectiveness of the mass-based particulate matter sampler, and comprised of the operation for obtaining the estimated total mass concentration including operations comprising:
   predicting an assumed density of the particulate matter;
   obtaining an assumed mass size distribution based on the non-mass-based size distribution and the assumed density of the particulate matter; and
   calculating the estimated total mass concentration from a formula $$M = \sum_i p_{(i)} c_{I(i)}$$

where M is the estimated total mass concentration, $p_{(i)}$ the sampling effectiveness of the mass-based particulate matter sampler in size interval i, and $C_{I(i)}$ the assumed mass distribution in size interval i.

10. The comprehensive particulate matter measurement system of claim 9, wherein the sampling effectiveness is simulated by a formula $$p_{(i)} = \frac{1}{1 + [D_{(i)}/D_{50}]^n}$$

where $p_{(i)}$ is the sampling effectiveness of the mass-based particulate matter sampler in size interval i, $D_{(i)}$ a representative aerodynamic diameter of particles in size interval i, $D_{50}$ a sampler cut point diameter, and n a parameter determining the steepness of the sampling effectiveness.

11. The comprehensive particulate matter measurement system of claim 9, comprised of the operation for obtaining the actual mass size distribution of the particulate matter by a formula $$c_{(i)} = c_{I(i)} \frac{C}{M}$$

where $c_{(i)}$ represents the actual mass size distribution of the particulate matter in size interval i, $c_{I(i)}$ the assumed mass size distribution of the particulate matter in size interval i, C the actual total mass concentration of the particulate matter, and M the estimated total mass concentration of the particulate matter.

12. The comprehensive particulate matter measurement system of claim 9, wherein the correct density of the particulate matter is derived from a formula, $\rho = \rho_A C / M$, where $\rho$ is the correct density of the particulate matter, $\rho_A$ the assumed density, C the actual total mass concentration, and M the estimated total mass concentration.

13. A machine readable storage medium providing instructions that cause the machine to perform operations to obtain a mass size distribution of particulate matter; the operations comprising:
   causing the machine to receive an actual total mass concentration of the particulate matter;
   causing the machine to receive a non-mass-based size distribution of the particulate matter;
   simulating the mass-based particulate matter sampler;
   obtaining an estimated total mass concentration of the particulate matter based on the non-mass-based size distribution of the particulate matter and the simulated mass-based particulate matter sampler;
   comparing the estimated total mass concentration with the actual total mass concentration;
   obtaining a correct density of the particulate matter; and
   obtaining an actual mass size distribution of the particulate matter from the density.

14. The machine readable storage medium of claim 13, comprised of the operation for causing the machine to receive an actual total mass concentration of the particulate matter including an operation for causing the machine to receive the actual total mass concentration of the particulate matter from a mass-based particulate matter sampler that is coupled to the machine.

15. The machine readable storage medium of claim 13, comprised of the operation for causing the machine to receive a size distribution of the particulate matter including an operation for causing the machine to receive the size distribution of the particulate matter from a particle sizing device that is coupled to the machine.

16. The machine readable storage medium of claim 13, comprised of the step of simulating the mass-based particulate matter sampler including a step of simulating a sampling effectiveness of the mass-based particulate matter sampler, and comprised of the operation for obtaining the estimated total mass concentration including operations comprising:
   predicting an assumed density of the particulate matter;
   obtaining an assumed mass size distribution based on the non-mass-based size distribution and the assumed density of the particulate matter; and
   calculating the estimated total mass concentration from a formula $$M = \sum_i p_{(i)} c_{I(i)}$$

where M is the estimated total mass concentration, $P_{(i)}$ the sampling effectiveness of the mass-based particulate matter sampler in size interval i, and $C_{I(a)}$ the assumed mass distribution in size interval i.

17. The machine readable storage medium of claim 16, wherein the sampling effectiveness is simulated by a formula $$p_{(i)} = \frac{1}{1 + [D_{(i)} / D_{50}]^n}$$

where $p_{(i)}$ is the sampling effectiveness of the mass-based particulate matter sampler in size interval i, $D_{(i)}$ a representative aerodynamic diameter of particles in size interval i, $D_{50}$ a sampler cut point diameter, and n a parameter determining the steepness of the sampling effectiveness.

18. The machine readable storage medium of claim 16, comprised of the operation for obtaining actual mass size distribution of particulate matter by a formula $$c_{(i)} = c_{I(i)} \frac{C}{M}$$

where $c_{(i)}$ represents the actual mass size distribution of the particulate matter in size interval i, $c_{I(i)}$ the assumed mass size distribution of the particulate mailer in size interval i, C the actual total mass concentration of the particulate matter, and M the estimated total mass concentration of the particulate matter.

19. The machine readable storage medium of claim 16, wherein the correct density of the particulate matter is derived from a formula, $\rho = \rho_A C / M$, where $\rho$ is the correct density of the particulate matter, $\rho_A$ the assumed density, C the actual total mass concentration, and M the estimated total mass concentration.

* * * * *